United States Patent [19]

Gabel

[11] Patent Number: 5,116,980
[45] Date of Patent: May 26, 1992

[54] BORON CONTAINING COMPOUNDS AND THEIR PREPARATION AND USE IN NEUTRON CAPTURE THERAPY

[75] Inventor: Detlef Gabel, Bremen, Fed. Rep. of Germany

[73] Assignee: The United States of America as represented by the United States Department of Energy, Washington, D.C.

[21] Appl. No.: 660,077

[22] Filed: Feb. 25, 1991

Related U.S. Application Data

[62] Division of Ser. No. 302,289, Jan. 27, 1989, Pat. No. 5,021,572.

[30] Foreign Application Priority Data

Jan. 29, 1988 [DE] Fed. Rep. of Germany ....... 3803063

[51] Int. Cl.⁵ .............................................. C07F 5/02
[52] U.S. Cl. .................................. 544/229; 540/541; 548/110; 568/5
[58] Field of Search ......................................... 544/229

[56] References Cited

U.S. PATENT DOCUMENTS 5,021,572 6/1991 Gabel ................................. 544/229

OTHER PUBLICATIONS

Allen, Proc. of First International Symposium on Neutron Capture Therapy, pp. 341-354 (1983).

Primary Examiner—Mukund J. Shah
Assistant Examiner—E. Bernhardt
Attorney, Agent, or Firm—Margaret C. Bogosian; James W. Weinberger; William R. Moser

[57] ABSTRACT

The present invention pertains to boron containing thiouracil derivatives, their method of preparations, and their use in the therapy of malignant melanoma using boron neutron capture therapy.

3 Claims, No Drawings

BORON CONTAINING COMPOUNDS AND THEIR PREPARATION AND USE IN NEUTRON CAPTURE THERAPY

This invention was made with Government support under Contract Number DE-AC02-76CH00016, between the U.S. Department of Energy and Associated Universities Inc. The Government has certain rights in the invention.

This is a division of co-pending application Ser. No. 302,289 filed Jan. 27, 1989, and now U.S. Pat. No. 5,021,572 issued Jun. 4, 1991.

BRIEF DESCRIPTION OF THE INVENTION

The present invention relates to new thiourea derivatives of the general formula

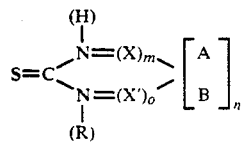

wherein:

A) R is hydrogen or an alkyl group containing from 1 to 8 carbon atoms, provided that where terminal double bonds originate from one of the two nitrogen atoms, R and/or the amide hydrogen is replaced;

B) X and X' are selected from the group consisting of

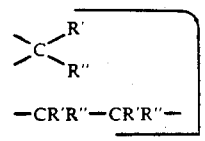   C atom(s) sp3-hybridized

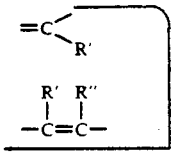   C atom(s) sp2-hybridized

   N atom sp3-hybridized

   N atom sp2-hybridized

   and

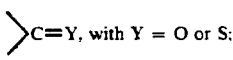   with Y = O or S;

C) m=0, 1 or 2 and o=0, 1 or 2;

D) 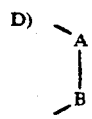 stands for a 1,2-dicarbaborane group, in which the 1- and 2-position of the carbon atoms correspond to A and B, and where n=0 or 1 but where not at the same time m, n, and o can all be zero, and where, if n=0, at least one of the groups R' and R" is a boron-containing group and the remaining groups R' and R" are hydrogen and/or an alkyl group with 1 to 8 carbon atoms and their salts with physiologically compatible organic and inorganic bases or acids.

The present invention also relates to methods for the preparation of the compounds of formula I, and their application in neutron capture therapy of malignant melanoma.

BACKGROUND OF THE INVENTION

Thioureas are known as substances which accumulate in malignant melanoma due to its active melanin synthesis.

Malignant melanoma is a tumor of melanocytes. Its incidence is especially high among the fair-skinned population. In most industrial nations its incidence is increasing.

Present treatment of melanoma consists of the surgical removal of the primary lesion. According to the histologically determined degree of classification, skin up to and including the regional lymph nodes are removed. Despite this, the five-year survival with melanomas grade II and higher, but also with melanomas grade I with high prognostic index (Kopf, *Cancer*, 59, 1236, 1987), is poor, as it apparently is not possible to remove all in-transit metastases of the skin and the lymph nodes.

Radiation treatment of the afflicted limbs, in order to sterilize these metastases with or without radical surgery, has not yet been successful (Kynaston, *Aust. N.Z. J. Surg.*, 48, 36, 1978).

The known radiotherapeutic modality of neutron capture therapy utilizes the property of boron-10 (which represents 20% of the naturally occurring nuclide mixture and can be enriched from it) to capture a thermal neutron with high probability, as compared to the other nuclides of the body, and disintegrate upon capture to a helium-4 and a lithium-7 particle. Each of these particles is capable of sterilizing a cell with a single event (Gabel, *Radiat. Res.* 68, 307, 1984).

Depending on the depth of the tumor and the energy spectrum of the neutron beam, at least 14 ppm boron-10 are necessary in the target tissue, for therapy to be successful, with a tumor-to-surrounding ratio of boron of around 10:1 (Fairchild and Bond, *Int. J. Radiation Oncol. Biol. Phys.*, 11, 831, 1985). For a thermal neutron beam and a tumor depth of 4 cm, tumor therapy is not possible with a boron ratio between tumor and surrounding tissue of 3:1 at any boron concentration; at a ratio of 10:1, 36 ppm boron are necessary.

Neutron capture therapy (NCT) differs from other radiotherapy modalities inasfar as an external beam produces a high radiation dose only where a chemical compound has accumulated prior to irradiation. It differs from other chemotherapy modalities inasfar as the compound accumulated expresses its tumoricidal action only in the field of the beam.

Coderre (*Cancer Research*, 48, 6313, 1988) has shown that p-dihydroxyborylphenylalanine (BPA) can accumulate physiologically in melanomas. Six hours after intraperitoneal injection, boron concentrations in the tumor of up to 30 ppm were found, with a tumor-to-blood and tumor-to-muscle ratio of around 5:1. After 24 hours, boron concentration in the tumor dropped and was too low for therapy.

Mishima (*Proc. 1st Int. Symp. NCT*, 355, 1984) has reported the treatment of melanoma in swine with neutron irradiation following peritoneal injection of a total of 10 g BPA.

Boronated thioureas, especially thiouracil derivatives, have been proposed for NCT by Fairchild (*Cancer Res.*, 42, 5126, 1982). However, except for some attempted syntheses by Wilson (Australia-Japan Workshop on Neutron Capture Therapy for Malignant Melanoma, 1986) no boronated analogue has been described in the literature. The major difficulty in synthesizing such derivatives lies in the properties of the dihydroxylboryl group, which is easily cleaved off organic molecules by acids as well as alkali. The dihydroxyboryl group has been introduced into NCT by Schinazi and Prusoff (*Tetrahedron Lett.*, 50, 4981, 1978; *J. Org. Chem.*, 50, 841, 1985).

The aim of the present invention is to provide stable boron-containing thiourea derivatives for neutron capture therapy, and to give procedures for their syntheses.

DETAILED DESCRIPTION OF THE INVENTION

Within the scope of this invention lie all cyclic thiourea derivatives, in which the cyclic portion, aside from the grouping

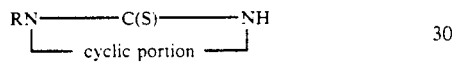

wherein R is H of lower alkyl
consists of carbon, nitrogen, oxygen, sulfur or combinations of these elements, wherein the cyclic portion can be saturated or unsaturated, and the number of the links connecting the two nitrogen atoms lies between 2 and 10, in which the carbon and/or nitrogen atoms of the cyclic part carry hydrogen atoms or where the hydrogen atoms are replaced by alkyl groups with 1 to 8 carbon atoms, and in which the cyclic part contains at least one boron-containing group. The boron containing group can be connected via a single or several bonds to different atoms of the cyclic part.

Representative compounds of the present invention include:

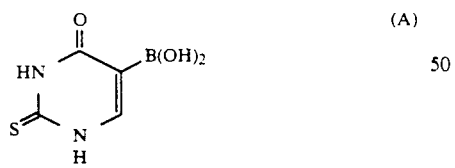

(A)

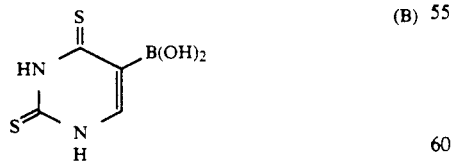

(B)

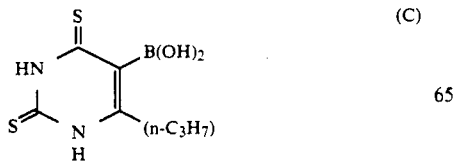

(C)

-continued

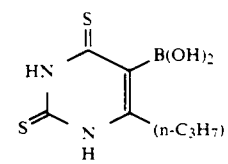

(D)

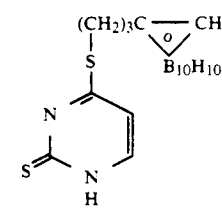

(E)

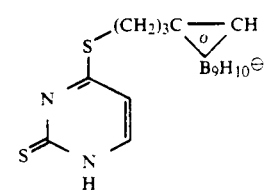

(F)

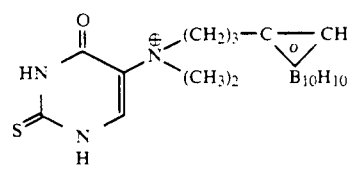

(G)

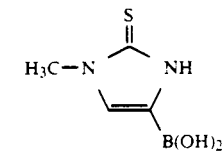

(H)

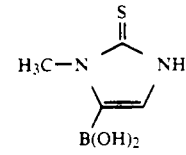

(I)

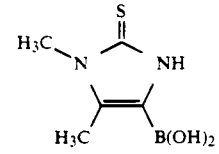

(K)

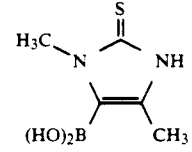

(L)

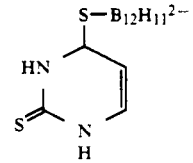

(M)

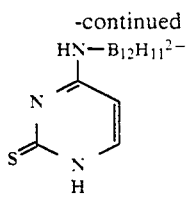
(N)

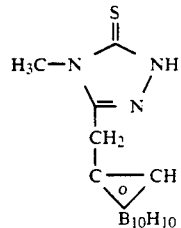
(O)

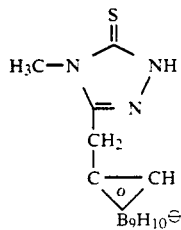
(P)

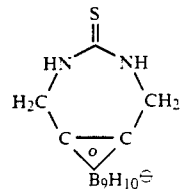
(Q)

The following are the complete chemical names for compounds A–O depicted above:
(A) 5-dihydroxyboryl-2-thiouracil
(B) 5-dihydroxyboryl-2,4-dithiouracil
(C) 5-dihydroxyboryl-6-propyl-2-thiouracil
(D) 5-dihydroxyboryl-6-propyl-2,4-dithiouracil
(E) 4-(3-carboranylpropyl)-thiyl-pyrimidine-2-thiol
(F) 4-(3-nidocarboranylpropyl)-thiyl-pyrimidine-2-thiol
(G) 5-(N-(3-carboranylpropyl)-N,N-dimethyl)amino-2-10 thiouracil
(H) 4-dihydroxyboryl-1-methylimidazole-2-thiol
(I) 5-dihydroxyboryl-1-methylimidazole-2-thiol
(K) 4-dihydroxyboryl-5-methyl-1-methylimidazol-2-thiol
(L) 5-dihydroxyboryl-4-methyl-1-methylimidazol-2-thiol
(M) 4-undecahydrododecaboranylthiyl-pyrimidin-2-thiol
(N) 4-undecahydrododecaboranylamino-pyrimidin-2-thiol
(O) 5-carboranylmethyl-1-methyl-2-thio-1,3,4-triazol
(P) 5-nidocarboranylmethyl-1-methyl-2-thio-1,3,4-triazol
(O) N,N'-thiocarbonyl-1,2-bis(aminomethyl)-nidocarboran.

Of the compounds of the present invention depicted by Formula I above, the most preferred materials are:
5-dihydroxyboryl-2-thiouracil
5-dihydroxyboryl-2,4-dithiouracil
5-dihydroxyborylboryl-6-propyl-2-thiouracil
5-dihydroxyboryl-2,4-dithiouracil
5-dihydroxyboryl-1-methylimidazole-2-thiol and 4-dihydroxyboryl-1-methylimidazole-2-thiol.

Cyclic thioureas according to the present invention can be obtained by: reacting, with boron compounds, a pre-formed cyclic thiourea derivative with suitable reactive groups, where the thiourea moiety of the end product is present as iso-thiourea; by reacting an open-chain thiourea moiety with a suitable boron-containing compound, followed by cyclization to the desired end product; or by reacting a suitable boron compound with a compound such that the thiourea moiety is introduced during the formation of the cyclic structure.

More specifically, thiourea derivatives of the general formula

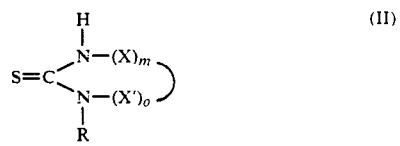
(II)

wherein R, X, X', m and o are as defined above are prepared when a compound of the general formula

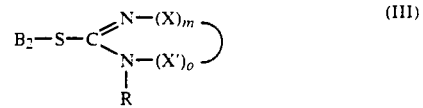
(III)

wherein R, X, X', m and o are as defined above in which the group(s) R' and R", which are the boron-containing groups in the final product, are the same as in the final product, or are present as dialkyloxy boryl groups, preferentially diothanolaminoboryl groups, is reacted with a Lewis acid and the dialkoxy groups, when present, are transformed hydrolytically to dihydroxyl boryl groups.

In the preparation of iso-thiourea derivatives exemplified by formula III above, where at least one of the groups R' and R" are —E—(alkylene)—z, with —E—=—O—, —S—, >NR''', and where R''' is hydrogen or alkyl with $C_1$ to $C_8$, and where the alkylene group contains 1 to 8 carbon atoms, and where Z is the 1,2-dicarba-closo-dodecaboranyl or 1,2-dicarba-nido-undecaboranyl group, preferably a compound of the general formula III, in which the position(s) that bear(s) the —E—(alkylene)—Z group in the final product, is(are) present as —OH, —SH, or >NR'''H, are reacted with the corresponding 1-(omega-haloalkyl)-1,2-dicarba-closo-dodecaborane

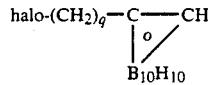

with halo=Cl, Br, I and q=1 to 8,
under neutral or basic conditions.

The preferred Lewis acids for use in the preparation of the compounds of formula II above include $AlBr_3$, $AlCl_3$, and $BBr_3$.

Thiourea derivatives of the general formula

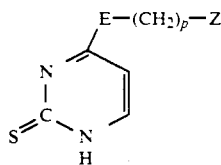

IIa wherein E= —O—, —S—, >NR''', with R'''=H or alkyl with 1 to 8 carbon atoms and p=1 to 8, and Z is the 1,2-dicarba-closo-dodecaboranyl group,
are prepared when a compound of the formula

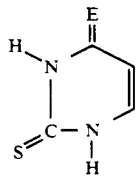

wherein E is as defined above is reacted with a 1-(omega-haloalkyl)-1,2-dicarbacloso-dodecaborane of the formula

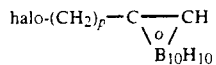

wherein the halogen is Cl, Br or I and p=1 to 8 under neutral or basic conditions.

Thiourea derivatives of the formula

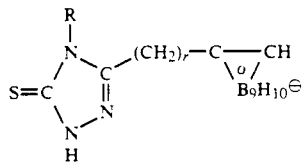 (IIb)

wherein R is as defined above and r=1 to 5 are prepared when a thiosoimicarbazide of the formula $$RHN-\underset{\underset{S}{\|}}{C}-NH-NH_2$$

wherein R is as defined above
is reacted with an omega-carboranyl acyl halide of the formula

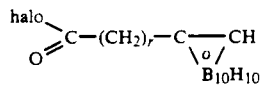

wherein halo and r are as defined above
and the reaction product is cyclized by action of a base.

Boron distribution in tissue was measured with 5-dihydroxyboryl-6-propyl-2-thiouracil (BPTU), and 5-dihydroxyboryl-2-thiouracil (BTU) using quantitative neutron capture radiography (Gabel, *Cancer Res.*, 47, 5451, 1987). BTU and BPTU exhibited several advantages compared to the compound p-boronophenylalanine, so far best suited for accumulation of boron in melanoma: a) BTU and BPTU accumulate in tumors for long time periods (days to weeks). For treatment of tumor it is advantageous if the accumulation once obtained can be retained, as several subsequent administrations of the compound will lead to higher accumulation. In addition, those cells can be loaded with boron that were, during the first administration, in a phase of their cell cycle not optimal for boron uptake. Also, the time between administration and irradiation can be changed in larger margins. A long period of accumulation is essential for a protracted or a fractionated irradiation; b) BTU and BPTU leave the other non-melanoma organs of the body rapidly. The compounds leave the body via kidney and gall bladder. Half times of BTU in blood and muscle are around 2 hours, for BPTU around 6 hours. Irradiation can thus be initiated shortly after the last administration; c) The compounds of this invention achieve boron concentration ratios between the tumor and its direct surrounding (blood, muscle, skin) of up to 50:1; and d) Maximum concentrations in the tumor of 100 ppm boron and more can be achieved.

Tables 1-4 show the distribution of BTU and BPTU in various melanomas.

TABLE 1

Distribution of 5-Dihydroxyboryl-2-thiouracil (Compound A) in Harding-Passey Melanoma

| Dose (mg/kg) | Time (hr) | Tumor (ppm) | Ratio Tumor To: | | |
|---|---|---|---|---|---|
| | | | Blood | Muscle | Brain |
| 300 | 3 | 40-80 | >5 | >5 | >8 |

TABLE 2

Distribution of 5-Dihydroxyboryl-6-propyl-2-thiouracil (Compound C) in B16 Melanoma

| Dose (mg/kg) | Time (hr) | Tumor (ppm) | Ratio Tumor To: | | |
|---|---|---|---|---|---|
| | | | Blood | Muscle | Brain |
| 300 | 12 | 3-10 | >10 | approx. 30 | approx. 20 |

TABLE 3

Distribution of 5-Dihydroxyboryl-2-thiouracil (Compound A) in Balb/cI Mice Carrying Harding-Passey Melanoma

| Dose (mg/kg) | Time (hr) | Tumor (ppm) | Ratio Tumor To: | | |
|---|---|---|---|---|---|
| | | | Blood | Muscle | Brain |
| 300 (t = 0) 240 (t = 3) | 12 | 80-100 | >5 | >8 | >15 |

TABLE 4

Distribution of 5-Dihydroxyboryl-6-propyl-2-thiouracil (Compound C) in C57bl Mice with B16 Melanoma

| Dose (mg/kg) | Time (hr) | Tumor (ppm) | Ratio Tumor To: | | |
|---|---|---|---|---|---|
| | | | Blood | Muscle | Brain |
| 190 | 4 | 4-90 (mean 41) | 10 | 5 | 4 |

The following examples are to illustrate the invention, especially concerning the procedures according to this invention, and the use of the resulting products. In this "carborane" designates the 1,2-dicarba, closo-dodecarborane group, "nidocarborane" the 1,2-dicarba-nido-undecarborate group derived from it. In the formulas, "Me" designates a methyl, and "Bz" a benzyl group.

EXAMPLE 1

The Introduction of the Benzylthio Protecting Group a) 2-Benzylthio-5-bromo-4-chloropyrimidine (I)

A suspension of 72 g of 0.242 moles (2-benzylthio)-5-bromouracil (Barrett, Goodman and Dittmer, *J. Amer. Chem. Soc.*, 70, 1753, 1948) is refluxed for 6 hours in 250 ml freshly distilled phosphorus oxychloride. The excess $POCl_3$ is removed on the rotary evaporator, 250 ml ice water are added to the residue, and extracted with diethyl ether. The ether layer is washed with a saturated solution of sodium bicarbonate, dried over magnesium sulfate, and the ether removed on the rotary evaporator. The residue is distilled (170° C., 0.03 mm). Yield 40 g=59%, white crystals, Mp 56°-57° C.

b) 2-Benzylthio-5-bromo-4-methoxypyrimidine (II)

A solution of 17 g (0.054 moles) of I in 50 ml dry toluene are added dropwise to a cooled suspension of 3.25 g (0.06 moles) sodium ethoxide, such that the temperature does not exceed 25° C. Stirring is continued for another 2 hours, NaCl is removed by filtering, and toluene is removed on the rotary evaporator. The residue is purified by distillation (160° C., 0.03 mm). Yield 13.5 g=80%, white crystals, Mp 48°-49° C.

c) 2,4-Bis-(benzylthio)-5-bromopyrimidine (V)

Benzylmercaptane (14.7 ml=0.125 moles) and 3 g (0.13 moles) sodium are heated to 80° C. in 200 ml dry toluene and stirred vigorously for 12-18 hours. The resulting thiolate suspension is cooled in an ice bath, and 14 g (0.062 moles) 5-bromo-2,4-dichloropyrimidine (Hilbert and Jansen, *J. Amer. Chem. Soc.*, 56, 134, 1934) are added dropwise such that the temperature does not exceed 25° C. The reaction mixture is stirred at room temperature overnight, and freed by filtration from NaCl and remaining thiolate. The filtrate is reduced on a rotary evaporator and purified by distillation (200° C., 0.03 mm). Yield 16.4 g=66%, white crystals, Mp 66°-67° C.

EXAMPLE 2

Preparation of Boron-containing Thiourea Derivatives

Ia) Diethanolamine derivatives of 2-benzylthio-5-dihydroxyboryl-4-methoxypyrimidine (III)

A 250-ml three-necked round-bottom flask, equipped with a low-temperature thermometer and a rubber septum, is flooded with nitrogen gas and then dried thoroughly with a heat gun. II (5 g-16 mmoles), dissolved in 150 ml dry, freshly distilled tetrahydrofurane, is injected into the RB flask through the septum. The solution is cooled to −100° C. in a cooling mixture of ethanol/liquid nitrogen. n-Butyl lithium (11 ml=17.5 mmoles) of a 1.6 molar solution in hexane and 5 ml (18.5 mmoles) tributylborate are filled into syringes and cooled to −80° C. in the cooling mixture. n-Butyl lithium is now injected into the RB flask over a period of 5 minutes. The temperature should not rise above −85° C. After 10 additional minutes of stirring, tributyl borate is injected into the flask. The reaction mixture is allowed to warm to room temperature over a period of 1.5 hours, and evaporated on the rotary evaporator. The residue is dissolved in 100 ml 2M NaOH and is extracted with 4×50 ml ether. The water layer is brought to pH=2 with concentrated HCl and again extracted with ether. A saturated solution of diethanolamine is added to the above ether extract, until no further precipitate is formed. The crystals are filtered and dissolved in little ethanol. Petrol ether (bp 35°-50° C.) is added until a slight cloudiness develops. The solution is allowed to stand for 3 hours, the precipitate is filtered off and dried at 100° C. Yield 3.5 g=63.4%, white crystals, Mp 185°-186° C.

b) 5-Dihydroxyboryl-2-thiouracil (A)

Five g (14.5 mmoles) of III are added slowly to a vigorously stirred solution of 15.5 g (58 mmoles) $AlBr_3$ in 100 ml dry toluene. The reaction mixture is stirred for 5 hours at 50°-60° C., and cooled. One hundred ml ice water are added slowly. The raw product is filtered off, dissolved in 75 ml 1 M NaOH, and the solution extracted with ether. Subsequently, the water layer is acidified to pH=2 with concentrated HCl, the precipitate is filtered off, and washed with acetone. It is recrystallized from ethanol. Yield 1.2 g=48.2%, white crystals. Mp>300° C.

| Elemental analysis $C_4H_5BN_2O_3S$ | | |
|---|---|---|
| | % | |
| | calc. | found |
| C | 27.94 | 28.19 |
| H | 2.93 | 3.19 |
| N | 16.28 | 16.21 |

2a) Diethanolamine derivative of 2,5-bis-(benzylthio)-5-dihydroxyborylpyrimidine (VI)

V [(6.45 g=16 mmoles, 11 ml (17.5 mmoles)] of a 1.6 molar solution of n-butyl lithium in n-hexane, and 5 ml (18.5 mmoles) tributylborate are reacted according to III. Yield 3.9 g=55.8%, white crystals, Mp 157°-158° C.

b) 5-Dihydroxyboryl-2,4-dithiouracil (B)

VI (6.33 g=14.5 mmoles) and 15.5 g (58 mmoles) $AlBr_3$ are reacted as described for A. The product is dissolved again in 3M NaOH, extracted with ether, acidified to pH=2 with concentrated HCl, and filtered. Yield 1.1 g=40.4%, yellowish crystals, Mp>300° C.

| Elemental analysis $C_4H_5BN_2O_2S_2 \times 0.5 H_2O$ | | |
|---|---|---|
| | % | |
| | calc. | found |
| C | 24.49 | 24.49 |
| H | 3.08 | 2.79 |
| N | 14.28 | 14.38 |

5-Dihydroxyboryl-6-propyl-2-thiouracil and 5-dihydroxyboryl-6-propyl-2,4-dithiouracil were prepared in an analogous manner.

3. Synthesis of 4-(3-carboranylpropyl)thlyl-pyrimidine-2-thiol (E)

4-Thiouracil (Mizumo, Ikehara and Watanabe, *Chem. Pharm. Bull.*, 10, 647, 1972) in dimethyl formamide is reacted with iodopropyl carborane (Zakharkin, Brattsev and Chapovskii, *J. Gen. Chem. USSR*, 35, 2149, 1965) to yield 4-(3-carboranylpropyl)thiyl-pyrimidine 2-ol. The chloro derivative is obtained with $POCl_3$ through methods known in the literature. Reaction to the 2-thiol derivative with thioureu is likewise achieved through methods known in the literature.

4. Synthesis of 4(5)-dihydroxyboryl-1-methylimidazolo-2-thiol (H/I)

2-Benzylthio-4(5)-iodo-1-methylimidazole is prepared from 2-benzylthio-4(5)-iodoimidazole (Hebner and Scholz, U.S. Pat. No. 2,654,761, 1951) with dimethyl sulfate. This is reacted in tetrahydrofurane at −85° C. with an equimolar amount of butyl lithium and then tributylborate. Further steps and removal of the benzyl protecting group is carried out in analogy to 5-dihydroxyboryl-2-thiouracil.

5. Synthesis of 4-undecahydrododecaboranylamino-pyrimidine 2-thiol (N)

2-Benzylthio-4-chloropyrimidine is reacted in DMF with sodium aminoundecahydrododecaborate (Nakagawa and Aono., Chem. Pharm. Bull., 24, 778, 1976). Removal of the benzyl group is achieved as described for 5-dihydroxyboryl-2-thiouracil.

In an analagous manner, 4-undecahydrododecaboranylthio pyrimidine 2-thiol is obtained upon reaction with disodium mercaptoundecahydrododecaborate.

6. Synthesis of 5-nidocarboranylmethyl-1-methyl-2-thio-1,3,4-triazol (P)

N-Methyl-thiosemicarbazide is reacted with 3-carboranyl acetyl chloride (Zakharkin, Chapovskii, Brattsev and Stanko, J. Gen. Chem. USSR, 36, 892, 1966) to N-methyl-N''-B-carboranyl acetyl thiosemicarbazine. The reaction product is cyclized with NaOH analogous to Kroger, Sattler and Beyer (Ann. Chem., 643, 128, 1961).

7. Synthesis of N,N'-thiocarbonyl-1,2-bis-(aminomethyl)-nidocarborane (O)

1,2-Bis-(aminomethyl)-nidocarborane (Zakharkin and Grebennikov, Izv. Akad. Nauk SSSR, Ser. Khim. 2019, 1966) is heated slowly with carbon disulfide in 50% ethanol/water under nitrogen according to Chau-Der Li, Mella and Sartorelli (J. Med. Chem., 24, 1989, 1981). After 1 hour, an equimolar amount of concentrated HCl is added, and the reaction mixture is worked up after refluxing overnight.

EXAMPLE 3

Examples of Use

1. Preparation of a Solution of 5-dihydroxyboryl-2-thiouracil for Intraperitoneal Injection 5-Dihydroxyboryl-2-thiouracil (50.4 mg) are dissolved in 10 ml 0.12M NaOH and adjusted to pH=7.8 with 0.12 m HCl. The solution is sterile filtered.

2. PREPARATION OF AN ORALLY ADMINISTRABLE FORM a) Five hundred mg 5-dihydroxyboryl-2-thiouracil are dissolved in 10 ml 1M tris-hydroxymethylaminomethane.

b) Mannitol (4.5 g) and 2 g methyl hydroxyethyl cellulose are mixed for approximately 3 minutes, passed through a sieve of a mesh diameter of 0.8 mm, and mixed again for 3 minutes. The obtained powder is wetted with the solution a) and mixed. The humid granulate is passed through a sieve with a mesh diameter of 1.25 mm, dried for 2 hours at 50° C. and 27 kPa (200 torr), passed through a sieve with a mesh diameter of 1.0 mm, and mixed for three minutes. The granulate obtained is mixed with 100 ml water p.i. and used within 5 minutes after preparation.

3. USE OF THE COMPOUND

Balb/c mice, carrying a subcutaneously transplanted Harding-Passey melanoma on their hind leg, are injected intraperitoneally 5 times, with 6 hour intervals, with the solution prepared according to Example 3 paragraph 1 above. The uptake in tumor is determined to 15-30 ppm with quantitative neutron capture radiography. The tumor is irradiated once with a neutron beam from a reactor, while the rest of the body is protected from thermal neutron by lithium fluoride embedded in epoxy resin. The growth of the tumor is measured daily over the course of several weeks. With a neutron dose of 8 MWxmin at the Medical Research Reactor at Brookhaven National Laboratory, it is found that the tumor does not grow in around half of the group treated; in the other half, tumor growth is observed only after 7 to 10 weeks. In the absence of boron, retardation of tumor growth is found only in the first three weeks after irradiation.

I claim:

1. A compound of the formula

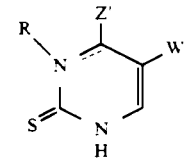

wherein R is hydrogen or an alkyl group having from 1 to 8 carbon atoms, provided that where a terminal double bond originates from the 3-position nitrogen atom, the R is absent from said 3-position nitrogen; Z' is =O, $-SB_{12}H_{11}^{-2}$, or $-NHB_{12}H_{11}^{-2}$, provided that if Z' is a boron containing group, the compound is in the form of a salt with a physiologically compatible cation; and W is hydrogen when Z' contains a boron group and W is

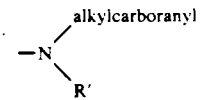

wherein the alkyl group has 1 to 7 carbon atoms and R' is hydrogen or alkyl having 1 to 7 carbon atoms, when Z' is =O
and their salts with physiologically compatible organic and inorganic bases or acids.

2. The salt of 5-(N-(3-carboranylpropyl)-N,N-dimethyl)amino-2-thiouracil with a physiologically compatible inorganic or organic acid.

3. The salt of 4-undecahydrododecaboranylthiyl-pyrimidin-2-thiol with a physiologically compatible inorganic organic base.

* * * * *